(12) United States Patent
Blain

(10) Patent No.: US 8,500,763 B2
(45) Date of Patent: Aug. 6, 2013

(54) SYSTEM AND METHOD FOR PROTECTING NEUROVASCULAR STRUCTURES

(75) Inventor: Jason Blain, Encinitas, CA (US)

(73) Assignee: Spinal Elemtents, Inc., Carlsbad, CA (US)

( * ) Notice: Subject to any disclaimer, the term of this patent is extended or adjusted under 35 U.S.C. 154(b) by 228 days.

(21) Appl. No.: 12/782,002

(22) Filed: May 18, 2010

(65) Prior Publication Data

US 2010/0228288 A1    Sep. 9, 2010

Related U.S. Application Data

(62) Division of application No. 11/055,162, filed on Feb. 10, 2005, now Pat. No. 7,744,612.

(60) Provisional application No. 60/543,212, filed on Feb. 10, 2004.

(51) Int. Cl.
    *A61B 17/08*    (2006.01)
(52) U.S. Cl.
    USPC .......................................................... 606/152
(58) Field of Classification Search
    USPC ........ 606/151–153; 607/117, 118; 623/17.11, 623/17.13, 17.16, 23.64, 23.74
    See application file for complete search history.

(56) References Cited

U.S. PATENT DOCUMENTS

| | | |
|---|---|---|
| 4,013,078 A | 3/1977 | Feild |
| 4,534,349 A | 8/1985 | Barrows |
| 4,573,471 A | 3/1986 | Rudner |
| 4,662,884 A | 5/1987 | Stensaas et al. |
| 4,669,474 A | 6/1987 | Barrows |
| 4,778,467 A | 10/1988 | Stensaas et al. |
| 4,870,966 A | 10/1989 | Dellon et al. |
| 4,883,618 A | 11/1989 | Barrows |
| 5,147,399 A | 9/1992 | Dellon et al. |
| 5,400,784 A | 3/1995 | Durand et al. |
| 5,487,756 A | 1/1996 | Kallesoe et al. |
| 6,102,921 A | 8/2000 | Zhu et al. |
| 6,106,558 A | 8/2000 | Picha |
| 6,600,956 B2 | 7/2003 | Maschino et al. |
| 6,999,819 B2 | 2/2006 | Swoyer et al. |
| 7,054,692 B1 | 5/2006 | Whitehurst et al. |

(Continued)

FOREIGN PATENT DOCUMENTS

| | | |
|---|---|---|
| EP | 1201202 | 5/2002 |
| EP | 1201256 | 5/2002 |
| GB | 2366736 | 3/2002 |
| WO | WO 02/096300 | 12/2002 |

OTHER PUBLICATIONS

Sep. 18, 2006 International Search Report and Written Opinion for International Application No. PCT/US05/04511, filed on Feb. 10, 2005.

(Continued)

*Primary Examiner* — Ryan Severson
*Assistant Examiner* — Ashley Fishback
(74) *Attorney, Agent, or Firm* — Knobbe, Martens, Olson & Bear, LLP

(57) ABSTRACT

Devices and methods for protecting the neurovascular structures about the vertebral column are provided. One embodiment of the invention comprises a neuroprotective stent or device adapted for placement in an intervertebral foramen of a vertebral column and configured to resist compression or impingement from surrounding structures or forces. The stent or device may further comprise a flange or hinge region to facilitate attachment of the device to the vertebrae or to facilitate insertion of the device in the foramen, respectively.

16 Claims, 14 Drawing Sheets

U.S. PATENT DOCUMENTS

2003/0204259 A1 10/2003 Goble et al.
2004/0111139 A1 6/2004 McCreery
2004/0199187 A1 10/2004 Loughran
2005/0192574 A1 9/2005 Blain
2006/0111768 A1 5/2006 Wessman et al.
2006/0129218 A1 6/2006 Swoyer et al.

OTHER PUBLICATIONS

Apr. 2, 2009 Office Action for Australian Application No. 2005211797 filed on Feb. 10, 2005.

Sep. 15, 2009 Office Action for Japanese Application No. 2006-553298 filed on Feb. 10, 2005.

Apr. 23, 2010 Office Action for Japanese Application No. 2006-553298 filed on Feb. 10, 2005.

Aug. 12, 2011 Office Action for Canadian Application No. 2,555,407 filed on Feb. 10, 2005.

Dec. 19, 2011 Office Action in Australian Application No. 2011200370.

Supplementary European Search Report dated Dec. 18, 2009 for Application No. EP 05723001, filed Feb. 10, 2005.

SYSTEM AND METHOD FOR PROTECTING NEUROVASCULAR STRUCTURES

CROSS-REFERENCE TO RELATED APPLICATIONS

The present application is a divisional of U.S. application Ser. No. 11/055,162 filed on Feb. 10, 2005, which claims priority under 35 U.S.C. §119(e) to U.S. Provisional Application No. 60/543,212 filed on Feb. 10, 2004, the disclosures of which are incorporated by reference herein in their entirety.

BACKGROUND OF THE INVENTION

1. Field of the Invention

The present invention relates generally to devices and methods for mechanically protecting neurovascular structures, and in particular a neural structure located in or about the spine.

2. Description of the Related Art

Traumatic, inflammatory and degenerative conditions of the spine can lead to severe pain and loss of mobility. According to some studies, back and spine-related musculoskeletal impairment are the leading causes of reduced workplace productivity in the United States. Pain resulting from some types of spinal impairment may originate from a variety of underlying pathologies and clinical conditions. Some of the most common sources of pain are related to disc herniation and spinal stenosis.

Disc herniation occurs when some of the disc material found between the vertebrae is displaced and bulges into the spinal canal. Disc herniation often occurs as the disc material weakens with aging, but may also result from trauma, hereditary factors, or a combination of these and other factors. The resulting pain may be localized to the region of impingement or may radiate to the body regions innervated by the impinged nerve. The common surgical procedure for treating disc herniation involves removal of the herniated portion. The surgical procedure may also involve removal of most of the disc material and the placement of a bone graft to promote fusion between the two vertebrae to stabilize that portion of the spine. Surgical screws, rods and spacers may also be used to fuse the spine, either alone or in conjunction with a bone graft.

Spinal stenosis encompasses a series of conditions where a bony portion of the vertebral column is applying pressure to one or more segments of the spinal cord or the nerves that exit from the spinal cord. The pressure may give rise to pain or numbness in regions of the body innervated by those nerves. One form of spinal stenosis involves a narrowing of the bony canal which contains the nerves or nerve roots exiting the spinal column. The bony canal or foramen is formed by bony structures of two adjoining vertebrae of the spine, and may become narrow for a variety of reasons. These reasons include but are not limited to the growth of bone spurs into the foramen, reductions in the relative spacing between two vertebrae from deterioration of the vertebral discs, fractures from trauma or osteoporosis, or from breakdown of the facet joints where the vertebrae articulate with one another. Treatment of spinal stenosis frequently requires surgery to remove a portion of the vertebral bone to create more space for the nerves. This removal of bone may be combined with spine fusion or partial removal of an intervertebral disc. Other less common conditions that may cause nerve impingement include inflammatory disorders of the spine and tumors in the vertebrae.

Notwithstanding the foregoing, there remains a need for improved methods and devices for treating the spine.

SUMMARY OF THE INVENTION

Devices and methods for protecting the neurovascular structures about the vertebral column are provided. One embodiment of the invention comprises a neuroprotective stent or device adapted for placement in an intervertebral foramen of a vertebral column and configured to resist compression or impingement from surrounding structures or forces. The stent or device may further comprise a flange or hinge region to facilitate attachment of the device to the vertebrae or to facilitate insertion of the device in the foramen, respectively.

One embodiment of the invention comprises a device for treating the spine, the device comprising a tubular body having a first end, a second end, an abluminal surface, a luminal surface, a lumen, a first edge, a second edge, and a hinge region, wherein the tubular body is adapted for positioning within an intervertebral foramen. The device may further comprise a flange, and the flange may comprise one or more through openings adapted for accepting a bone screw. In some embodiments, the tubular body comprises a material selected from the group consisting of polymers, polyetheretherketone (PEEK), polyetherketoneketone (PEKK), polyethylene, fluoropolymers, elastomers, ceramics, zirconia, alumina, silicon nitride; metal(s), titanium, titanium alloy, cobalt chromium, stainless steel, and combinations of these materials. In one embodiment, the hinge region comprises at least one region of reduced wall thickness of the tubular body.

In another embodiment of the invention, a device for treating the spine is provided, comprising a tubular body, the tubular body comprising a first end, a second end, an abluminal surface, a luminal surface, a lumen, a first edge, and a second edge, wherein the tubular body is adapted for positioning within an intervertebral foramen and wherein the first edge and second edge have interlockable configurations. The device may further comprise a locking element and wherein the interlockable configurations of the first edge and second edge each comprise alignable openings adapted to accept the locking element.

In one embodiment of the invention, a device for treating the spine is provided, comprising a tubular body, the tubular body comprising a first end, a second end, an abluminal surface, a luminal surface, a lumen adapted for accepting a nerve, a first edge, and a second edge, wherein the tubular body is adapted for positioning within an intervertebral foramen and wherein the tubular body comprises a material selected from the group consisting of polymers, polyetheretherketone (PEEK), polyetherketoneketone (PEKK), polyethylene, fluoropolymers, elastomers, ceramics, zirconia, alumina, silicon nitride; metal(s), titanium, titanium alloy, cobalt chromium, stainless steel, and combinations of these materials. The tubular body may further comprise a hinge region. In some embodiments, the first edge and second edge have interlockable configurations. In one embodiment, the first end of the tubular body has a flared configuration.

In one embodiment of the invention, another device for treating the spine is provided, comprising a tubular body having a first end, a second end, an abluminal surface, a luminal surface, a lumen adapted for accepting a nerve, a first edge, a second edge and a longitudinal opening between the first edge and second edge; and a spacer, wherein the tubular body is adapted for positioning within an intervertebral foramen. In one embodiment, the spacer has a first groove configured to accept the first edge of the tubular body and a second groove configured to accept the second edge of the tubular body.

In another embodiment of the invention, a device for treating the spine is provided, comprising a tubular body having a first end, a second end, an abluminal surface, a luminal surface, a lumen, a first edge and a second edge, wherein the tubular body is adapted for positioning within an intervertebral foramen and wherein the tubular body is configured to resist compression forces from spinal structures. The tubular body may be a stent structure. The spinal structures may comprise an intervertebral disc and/or a vertebra.

One embodiment of the invention comprises a method for treating a spine, the method comprising providing a tubular body having a lumen and adapted for placement within an intervertebral foramen, wherein the tubular body is configured to resist compression forces from spinal structures and inserting the tubular body into the intervertebral foramen. The method may further comprise providing a spacer, inserting the spacer into the intervertebral foramen and expanding the tubular body. In a further embodiment of the invention, the step of providing a tubular body comprises providing a stent structure.

BRIEF DESCRIPTION OF THE DRAWINGS

The structure and method of using the invention will be better understood with the following detailed description of embodiments of the invention, along with the accompanying illustrations, in which.

DETAILED DESCRIPTION OF SPECIFIC EMBODIMENTS

The present invention relates to a treatment for conditions of the spine. In some embodiments of the invention, the treatment allows the patient to maintain mobility at the treated portion of the spine, unlike traditional spine surgeries or implanted spinal hardware. For example, certain embodiments allow restoration and/or protection of the neural space by mechanically alleviating or reducing the pressure exerted onto neural structures which may reduce or eliminate pain associated with nerve impingement. In some embodiments, the device shields nerves from compression by surrounding structures that may cause pain. In one embodiment, the device prevents the development of postoperative adhesions or scar tissue between a patient's spinal nerves and other spinal tissues by providing an intervening barrier. An embodiment of the invention may also be used to protect other structures in neurovascular bundles, including blood vessels and/or lymphatic ducts.

An embodiment of the invention may also be used as an adjunct to discectomy procedures. If the disc re-herniates, the device may provide protection against disc material that may impinge on spinal nerves.

A. Anatomy of the Spine

Figure 1:
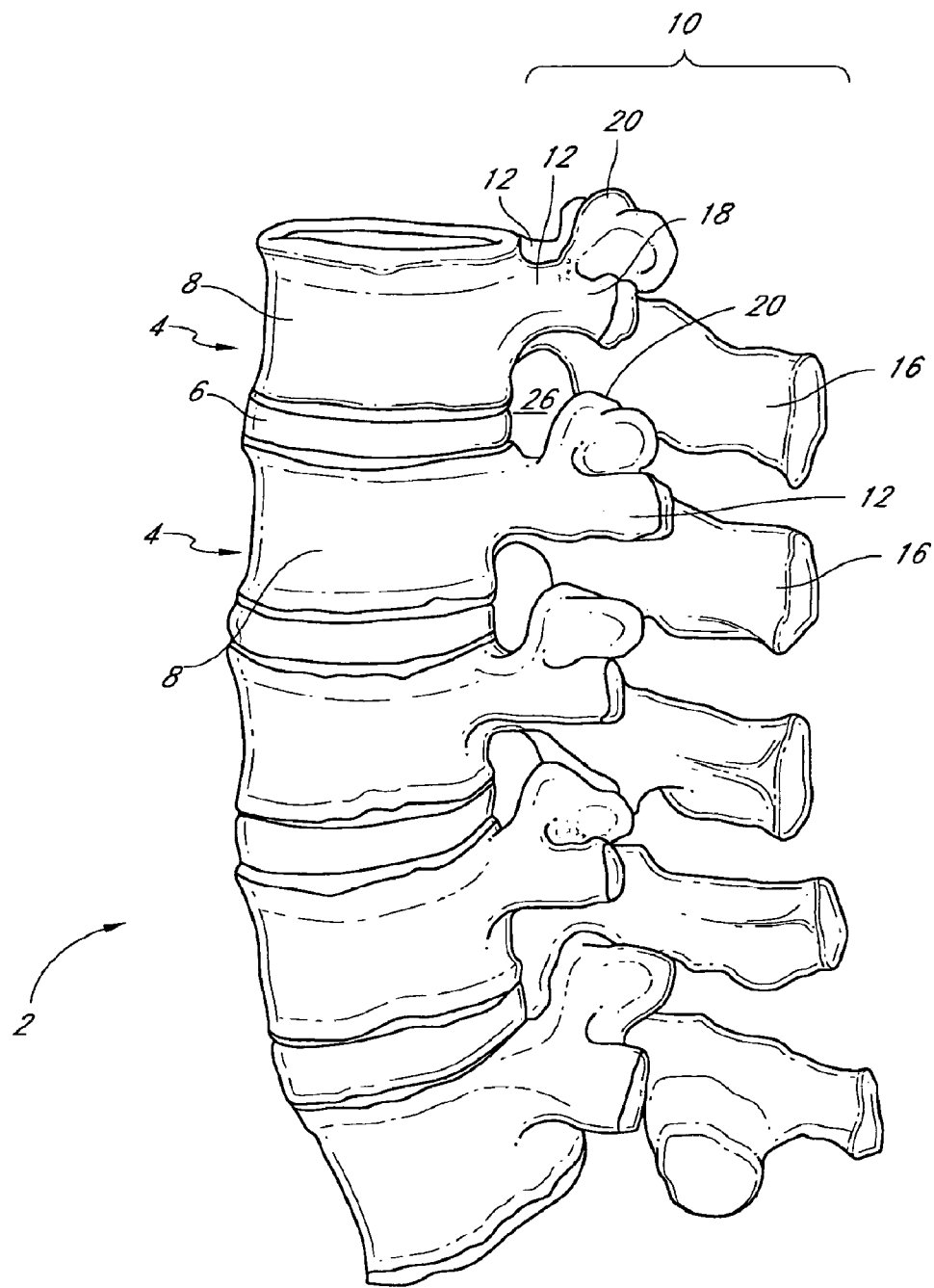
FIG. 1 is a lateral elevational view of a portion of the vertebral column.
Figure 2:
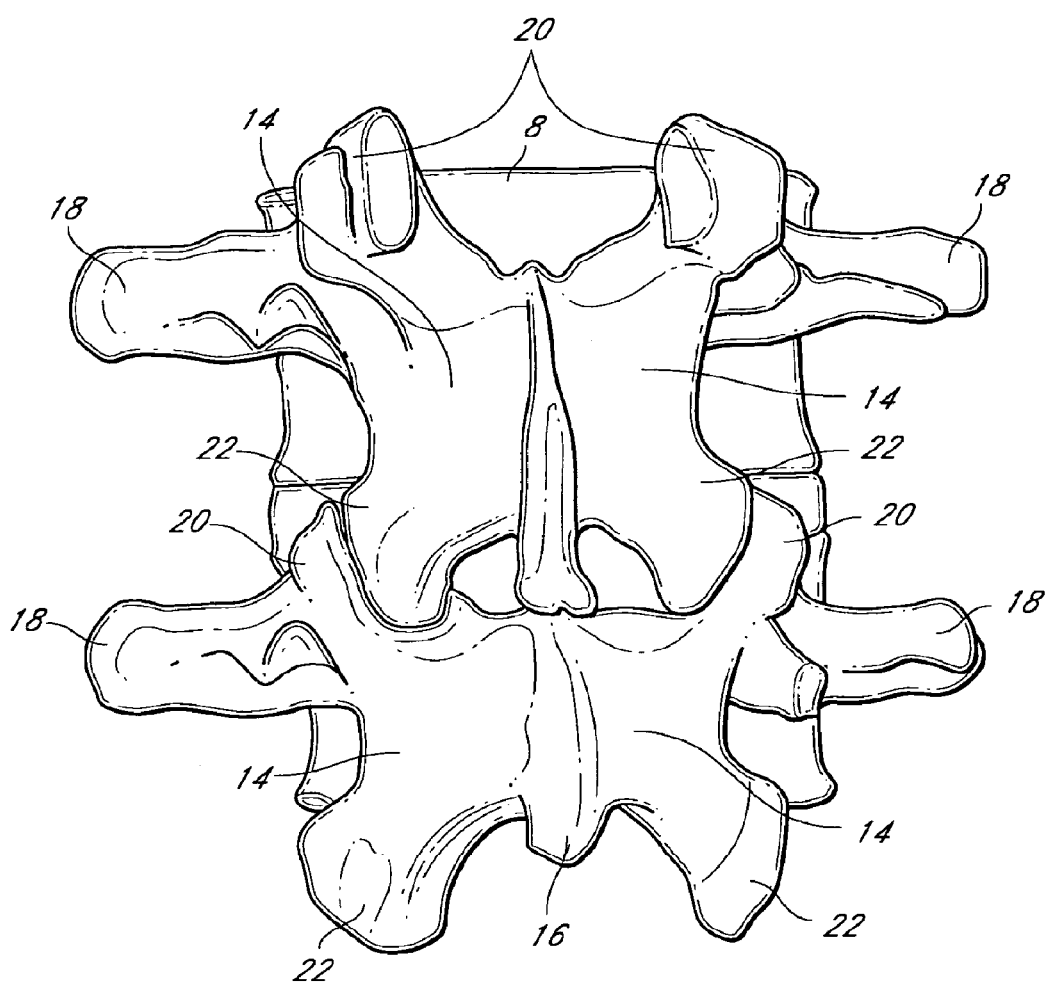
FIG. 2 is a schematic posterior elevational view of two lumbar vertebrae.
Figure 3:
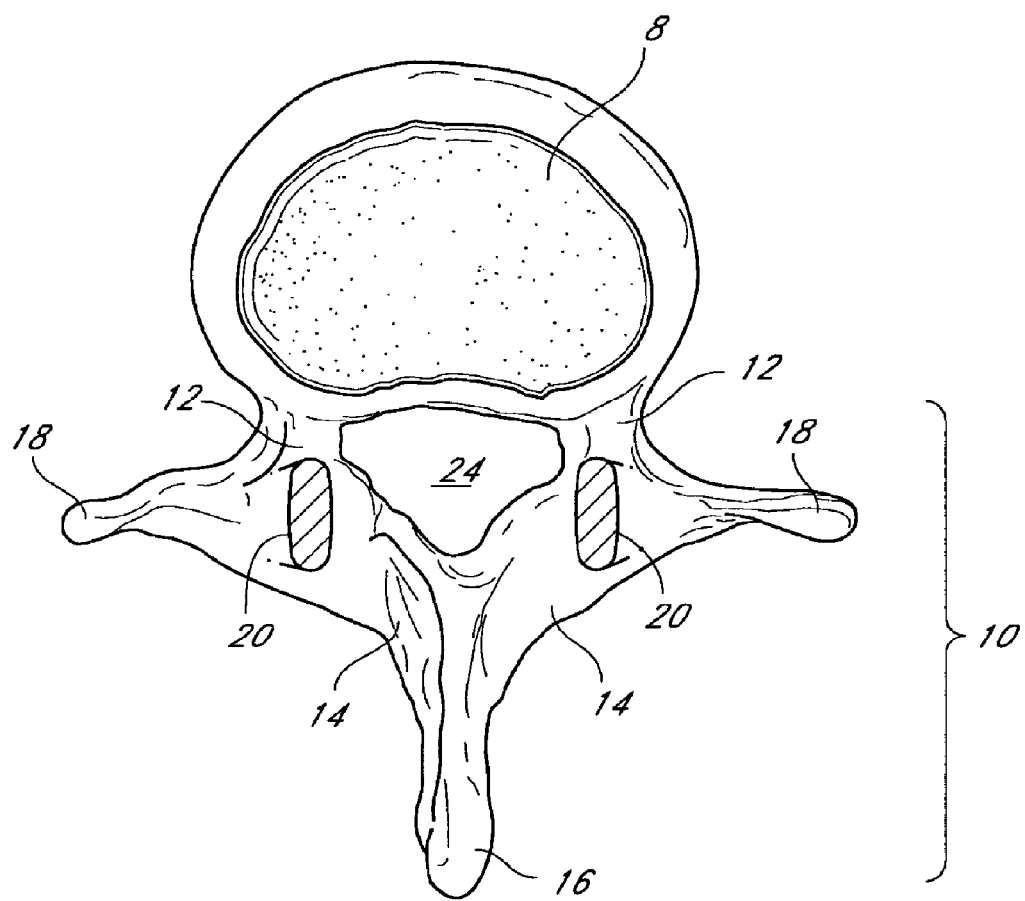
FIG. 3 is a schematic superior elevational view of a lumbar vertebra.

As shown in FIGS. 1 and 2, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae 4. Each vertebra 4 includes an anterior body 8 and a posterior arch 10. Referring to FIGS. 2 and 3, the posterior arch 10 comprises two pedicles 12 and two laminae 14 that join posteriorly to form a spinous process 16. Projecting from each side of the posterior arch 10 is a transverse 18, superior 20 and inferior articular process 22. FIG. 3 depicts the spinal canal 24 that contains the spinal cord (not shown) and is surrounded by the pedicles 12 and laminae 14. Referring back to FIG. 1, the pedicles 12 of each pair of adjacent vertebrae 4 form an intervertebral foramen 26.

Figure 4:
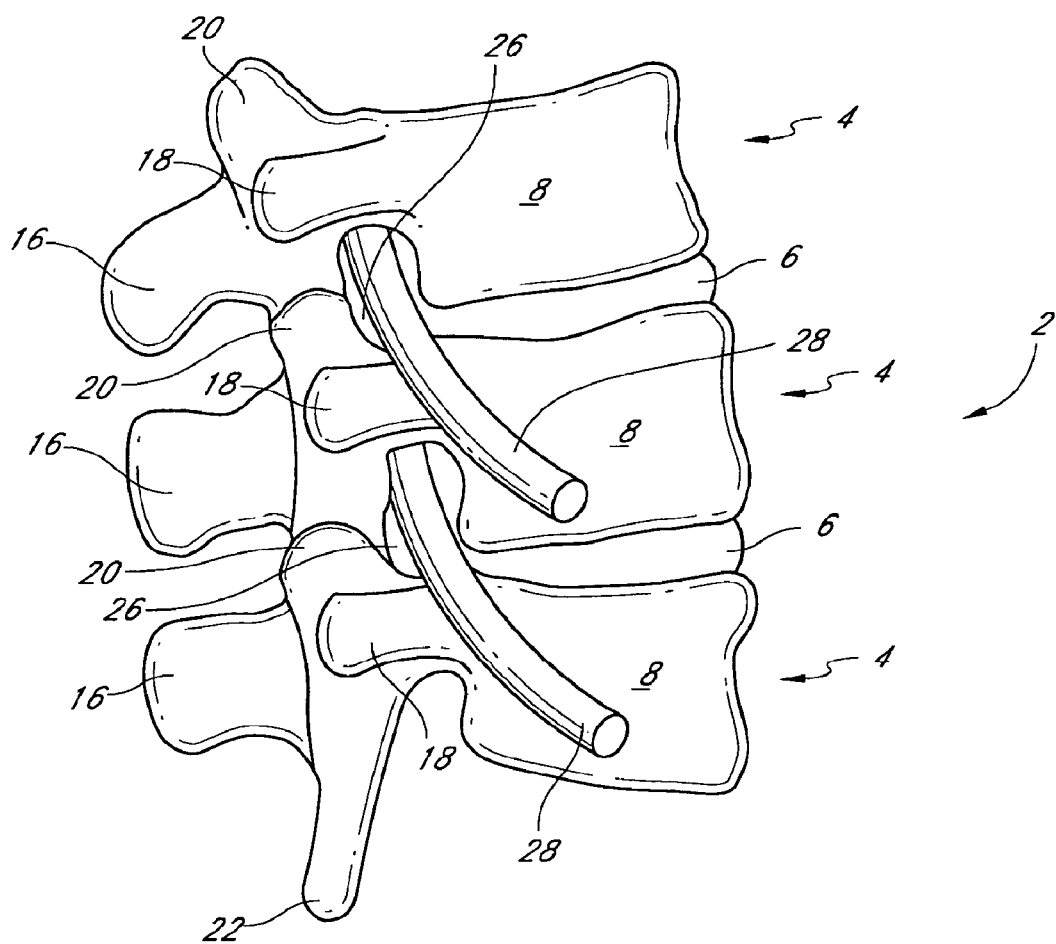
FIG. 4 is a schematic lateral elevational view of a portion of the lumbar spine with spinal nerves in the intervertebral foramina.
Figure 5:
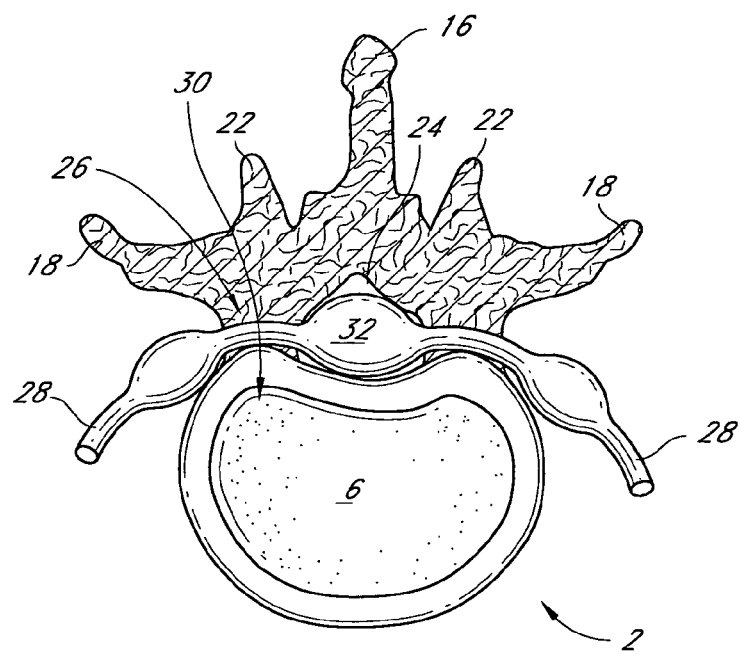
FIG. 5 is a schematic transverse cross-sectional view of a spine with nerve impingement by a vertebral disc.
Figure 6:
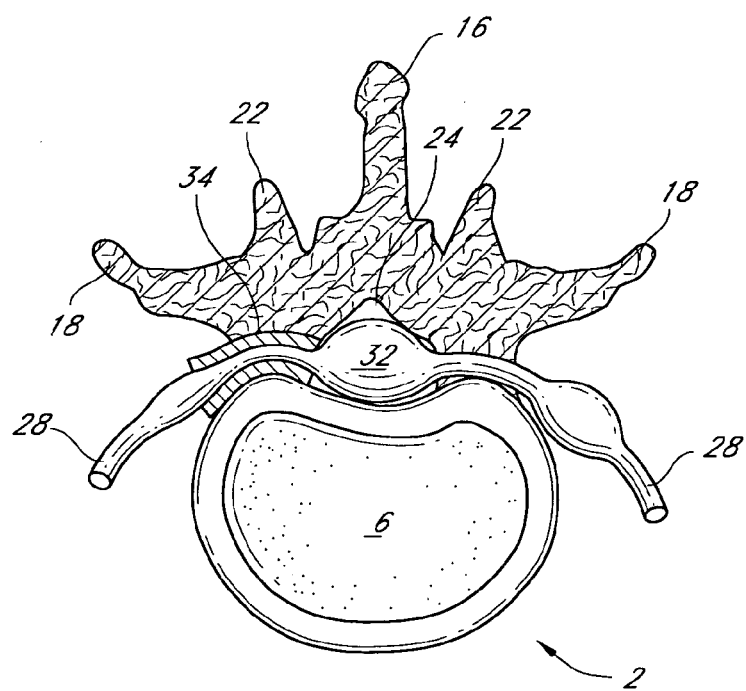
FIG. 6 depicts the spine from FIG. 5 with one embodiment of the invention placed in the intervertebral foramen.

FIG. 4 depicts a portion of the vertebral column 2 with spinal nerves 28 exiting from the intervertebral foramina 26 formed by the pedicles 12 of adjacent vertebrae 4. FIG. 5 depicts a transverse cross-sectional view of the vertebral column 2 through the intervertebral foramina 26 wherein the vertebral disc 6 has a herniation or bulge 30 posteriorly on one side and has impinged a spinal nerve root 28 exiting the spinal cord 32. By placing a neuroprotective device 34 in the affected intervertebral foramen 26, as illustrated in FIG. 6, the device 34 is able to relieve pressure exerted on the nerve root 28 by the bulge 30 in the vertebral disc 6 and may reduce the inflammation and pain associated with nerve impingement. In addition to protecting the nerve root 28 from disc hernations 30 or bone spurs, the device 34 may also protect the nerve root 28 from postsurgical adhesions or scar tissue that develop from other spinal surgeries. Postsurgical adhesions or scar tissue may also cause nerve impingement or nerve irritation.

Figure 7:
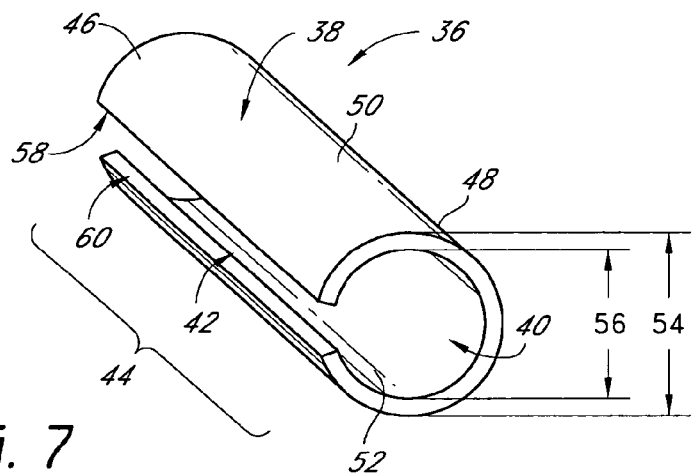
FIG. 7 illustrates one embodiment of the invention comprising a cylindrical tubular body.

Referring to FIG. 7, in one embodiment of the invention, the neuroprotective device 36 comprises a tubular body 38 with a lumen 40 and a longitudinal seam or opening 42 along the longitudinal length 44 of the tubular body 38. In one embodiment, the tubular body 38 comprises a stent structure. The tubular body 38 has a first end 46, a second end 48, an abluminal surface 50, a luminal surface 52, an outer diameter 54, an inner diameter 56, a first edge 58 and a second edge 60 about the longitudinal opening 42. In some embodiments, the device 36 has an outer diameter 54 in the range of about 0.5 mm to about 10 mm, and preferably about 3 mm to about 5 mm. The inner diameter 56 of the device 36 is in range of about 0.4 mm to about 9.9 mm, and preferably about 2 mm to about 4 mm.

Figure 8:
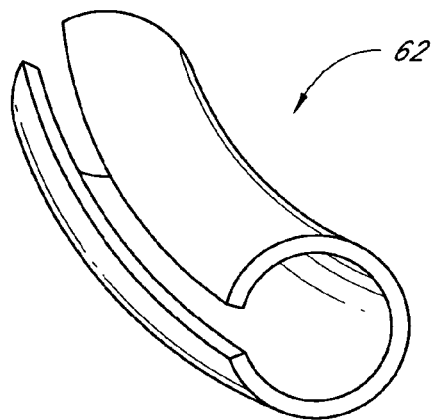
FIG. 8 is another embodiment of the invention comprising a curved tubular body.

The neuroprotective device 36 may have a generally linear configuration as shown in FIG. 7, or it may have a non-linear configuration. FIG. 8 depicts one embodiment of a non-linear configuration comprising a curved tubular body 62. A non-linear device may be better fitted to a particular patient's anatomy than a device 36 with a linear configuration.

Figure 9:
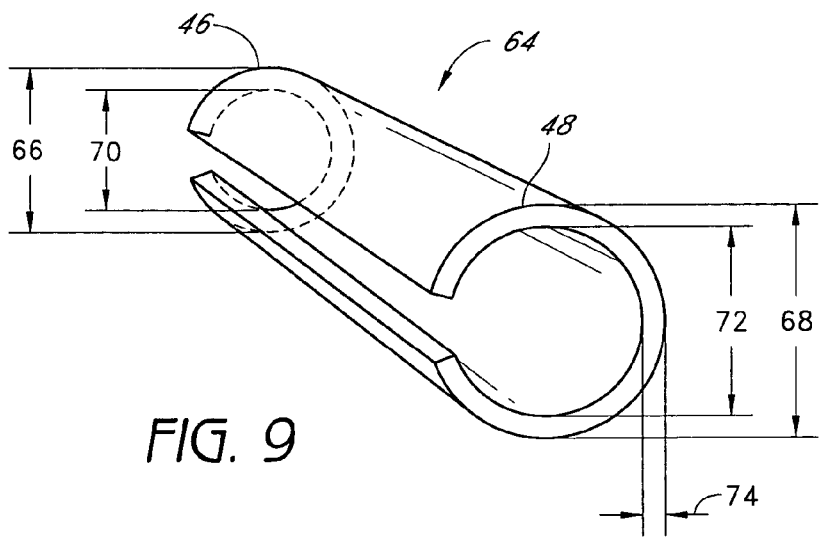
FIG. 9 is another embodiment of the invention comprising a tapered tubular body.
Figure 10:
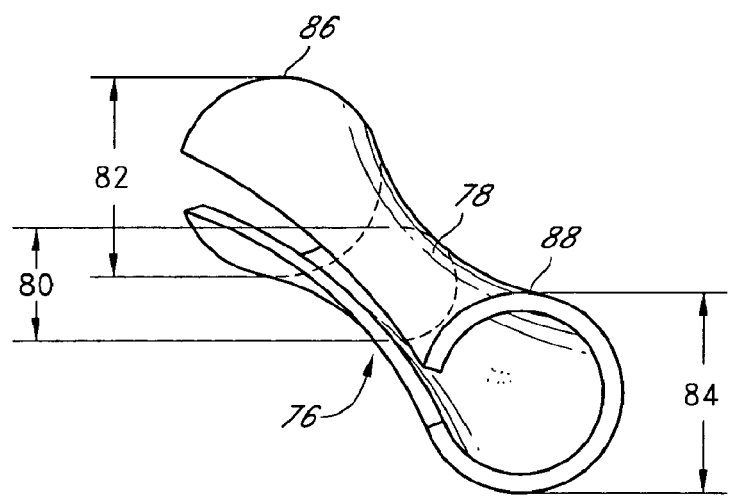
FIG. 10 is another embodiment of the invention comprising a dual-flared tubular body.

In some embodiments of the invention, the device 36 has a generally cylindrical shape, as depicted in FIG. 7, with a generally constant outer diameter 54 and inner diameter 56 along its longitudinal length 44. In other embodiments, either or both the outer diameter 54 and the inner diameter 56 of the device 36 can vary along the longitudinal length 44. FIG. 9 depicts one embodiment of the device 64 having a tapered outer diameter where the outer diameter 66 at the first end 46 is smaller than the outer diameter 68 at the second end 48. Such a configuration may facilitate insertion of the device 64 into the foramen 26. The inner diameters 70, 72 at the first end 46 and second end 48, respectively, of the device 64 may or may not change proportionately with the change in the outer diameters 66, 68. The wall thickness 74 of the device need not be constant at any point along the device 64. In some embodiments of the invention, the wall thickness 74 may be varied to provide augment the structural resistance to directional deformation forces that may affect the protected nerve 28. In another embodiment of the invention depicted in FIG. 10, the tubular body 76 comprises a middle section 78 having an outer diameter 80 that is less than the outer diameters 82, 84 at the first end 86 and second end 88 of the tubular body 76, respectively. The flared first and second ends 86, 88 may assist in stabilizing the position of the tubular body 76 by resisting slippage or displacement of the tubular body 76 out of the foramen 26.

Figure 11:
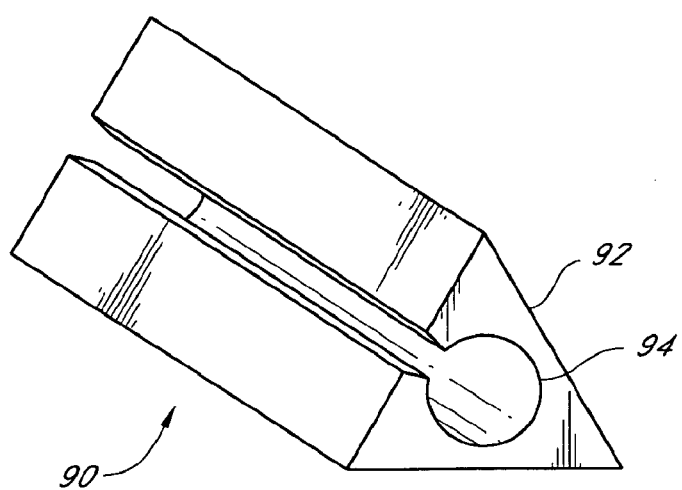
FIG. 11 depicts another embodiment comprising a tubular body having a triangular outer cross section with a circular lumen.

Although the general cross sectional shape of the device 36 depicted in FIG. 7 is a circular C-shape, the cross-sectional shape of the device 36 may be any of a variety of shapes, including triangular, oval, square, polygonal, trapezoid or any other shape. The general cross-sectional shape of the device may vary along the longitudinal length of the device and the general cross-sectional shape of the outer diameter and the lumen need not be the same. FIG. 11 depicts a neuroprotective device 90 having a linear configuration with a triangular outer cross section 92 and a lumen 94 having a circular cross section.

Figure 12:
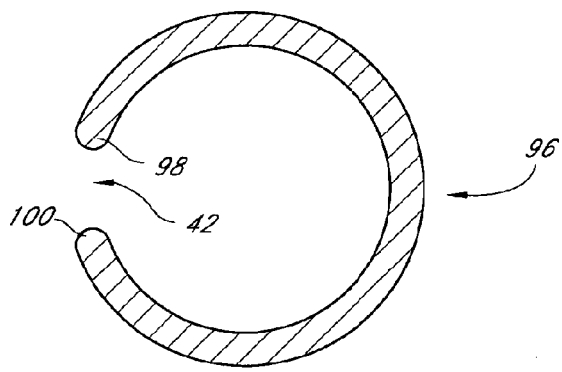
FIG. 12 is a cross sectional view through one embodiment of the invention with rounded edges.

In some embodiments of the invention, the first and second edges 58, 60 of the tubular body 38 may be squared or flat, as illustrated in FIG. 7, but in other embodiments, the first and second edges of the tubular body may have any of a variety of configurations. FIG. 12 depicts a cross sectional view of one embodiment of the invention wherein the tubular body 96 comprises rounded first and second edges 98, 100. The configuration need not be the same for the first and second edges 98, 100 and may also change along the longitudinal length of the tubular body 96. In some embodiments of the invention, the design and materials of the tubular body 96 are selected such that the tubular body 96 is configured to resist narrowing or closure of the longitudinal seam or opening 42 along the length of the tubular body 96 after implantation. In other embodiments of the invention, the tubular body 96 is configured to partially bend after implantation such that the first and second edges 98, 100 of the tubular body 96 contact along at least a portion of the longitudinal length of the seam or opening 42.

Figure 13:
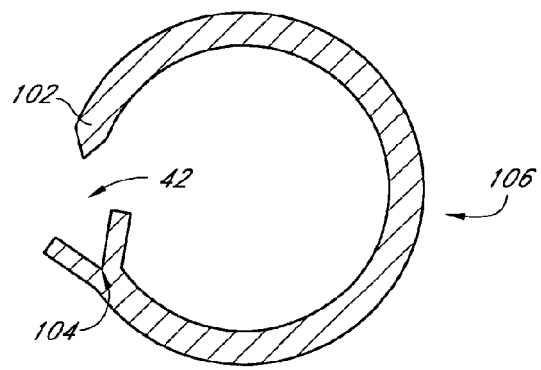
FIG. 13 is a cross sectional view through another embodiment of the invention having complementary edges.

Referring to FIG. 13, in some embodiments, the first and second edges 102, 104 of the tubular body 106 have complementary shapes that are capable of forming an interfit to resist further collapse or slippage between the first and second edges 102, 104. FIG. 13 illustrates one embodiment wherein the second edge 104 of the device comprises a Y-shaped cross sectional configuration adapted to accept a pointed first edge 102 of the tubular body 106. The Y-shaped cross section of the second edge 104 provides a broader contact surface area to reduce the risk that the first edge 102 may slip past the second edge 104 as compressive forces causes narrowing or closure of the longitudinal opening 42. One skilled in the art will understand that the first and/or second edges 102, 104 of the tubular body 96 may be configured with any of a variety of complementary configurations to reduce the risk of slippage between the edges and/or to resist collapse of the tubular body 96 generally. In some embodiments, a locking interfit may also be formed by the first and second edges of the tubular body.

Figure 14:
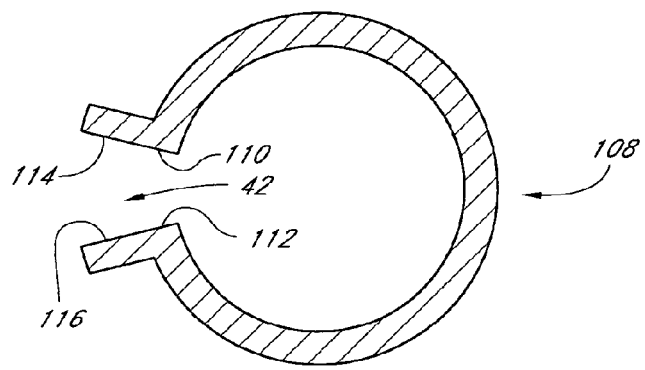
FIG. 14 is a cross sectional view through another embodiment of the invention having radially outward lipped edges.

In one embodiment of the tubular body 108, shown in FIG. 14, the first edge 110 and second edge 112 of the tubular body 108 each comprise a lip 114, 116 extending radially outward from the respective edges 110, 112 that provide a larger and more stable contact surface area for each edge 110, 112. The width of the lips 114, 116 also reduces the risk that either edge 110, 112 can slip past the other edge 110, 112. The lips 114, 116 need not be present along the entire length of the longitudinal opening 42. Optionally, paired openings may be provided in the lips 114, 116 to allow the lips 114, 116 to be fastened together with a screw or other fastener.

Figure 15:
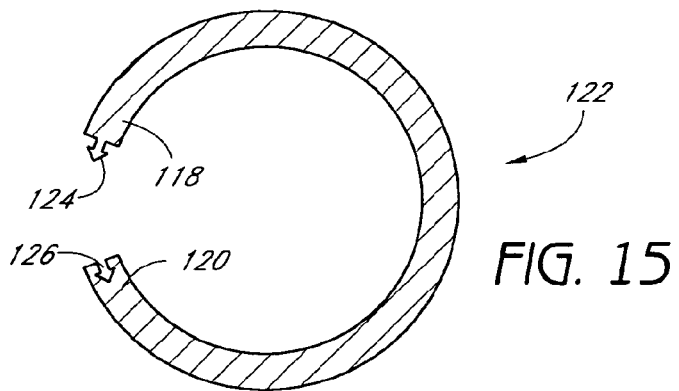
FIG. 15 is a cross sectional view through another embodiment of the invention having interlocking edges.

FIG. 15 depicts one embodiment of the invention comprising an interlocking complementary fit between the first edge 118 and second edge 120 of the tubular body 122, with the first edge 118 having a male member 124 and the second edge 120 having a female receiving site 126 for the male member 124.

Figure 16A:
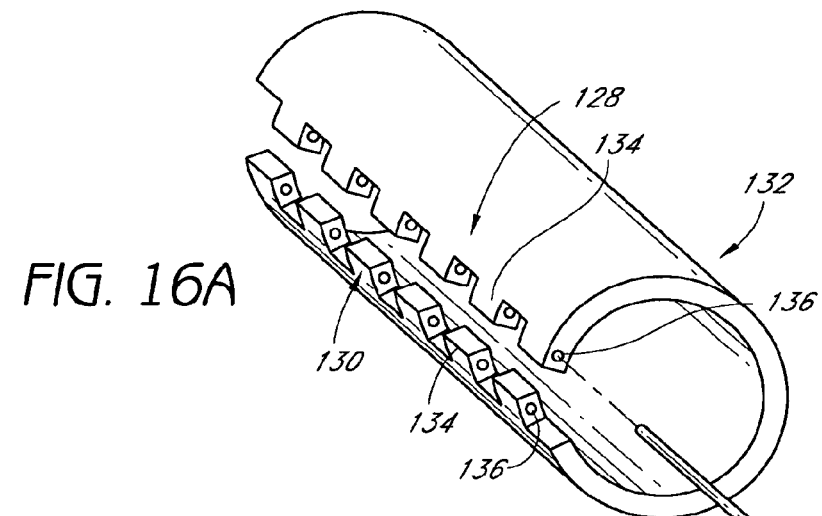
FIGS. 16A and 16B are oblique elevational views of one embodiment of the invention with a locking element.
Figure 16B:
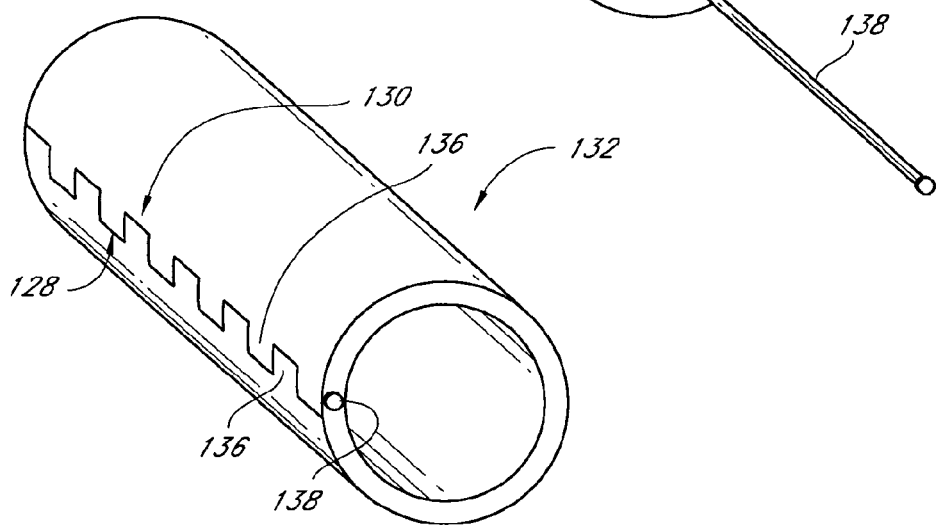

FIGS. 16A and 16B depict an embodiment of the invention with an interlockable complementary fit between the first edge 128 and second edge 130 of the tubular body 132, comprising complementary alternating protrusions 134 configured with longitudinally oriented lumens 136 that align when the protrusions 134 are in contact with one another. A separate locking element 138 may be inserted through the lumen to resist separation of the edges 128, 130. In a further embodiment of the invention, the tubular body has two longitudinal portions separated by two longitudinal seams, each portion capable of forming an interlocking fit with the other portion.

Figure 17:
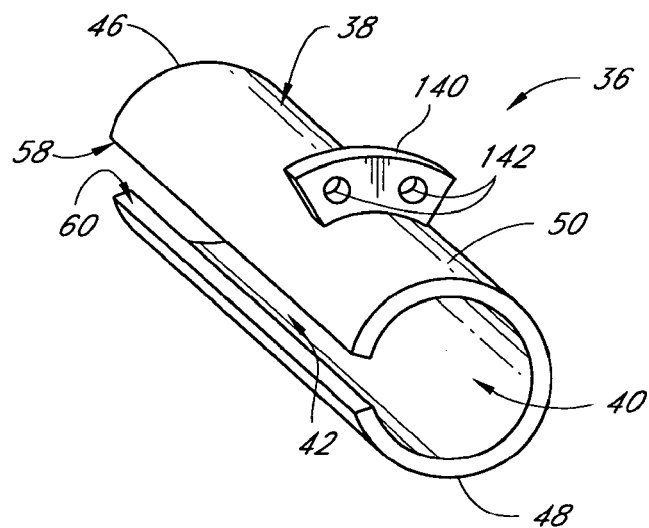
FIG. 17 illustrates one embodiment of the device having a flange.

In some embodiments of the invention, illustrated in FIG. 17, one or more flanges 140 may be provided along the abluminal surface 50 of the device 36. Each flange 140 may occupy a portion or all of a given circumference of the tubular body 38. In other embodiments, the flange may be oriented differently to allow attachment of the device 36 onto the transverse process or other structure of a vertebra 4. Each flange 140 may be located anywhere along the length of the tubular body 38, but is preferably located at the position which provides the expected insertion depth of the tubular body 38 into the foramen 26. Thus, the flange 140 may assist the surgeon in positioning the tubular body 38 in a desired location within the foramen 26. In some embodiments, the flange 140 comprises one or more through openings 142 capable of accepting a fixation component, such as a bone screw, for attaching the device 36 to a bony surface. In some embodiments, the flange 140 comprises a material or configuration that provides some malleability to allow the flange 140 to at least partially conform the flange 140 to the bony structure to which it is attached. In some embodiments of the invention, the flange 140 alone, without any openings, is sufficient to maintain the device 36 at the desired location.

Figure 18:
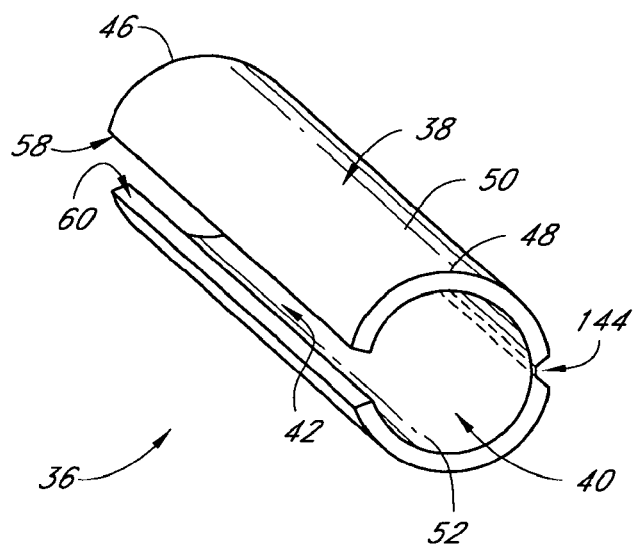
FIG. 18 depicts one embodiment of the device having a living hinge.

Referring to FIG. 18, in some embodiments of the invention, the tubular body 38 of the device 36 may have one or more regions 144 of reduced wall thickness to facilitate at least partial narrowing or widening of the longitudinal opening 42. Typically, the region or regions of reduced wall thickness comprise a full-length longitudinal hinge or groove 144 on the abluminal surface 50 and/or luminal surface 52 of the tubular body 38 that is generally about 180 degrees opposite the position of the longitudinal opening 42. In other embodiments, however, the region or regions of reduced wall thickness occupy only a portion of the longitudinal length of the tubular body 38 and/or are located at a position less about 180 degrees from the longitudinal opening 42 of the tubular body 38. In another embodiment of the invention, the tubular body 38 comprises a mechanical hinge along the length of the device 36 to allow at least partial opening and closing of the longitudinal opening 42.

Figure 19A:
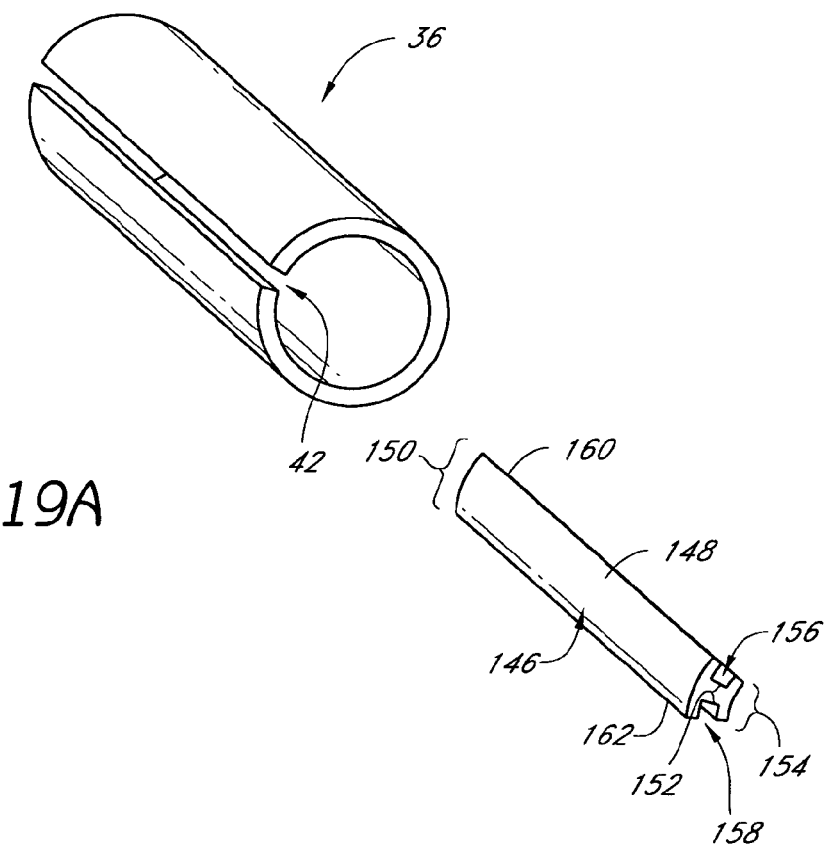
FIGS. 19A and 19B a neuroprotective device with a spacer.
Figure 19B:
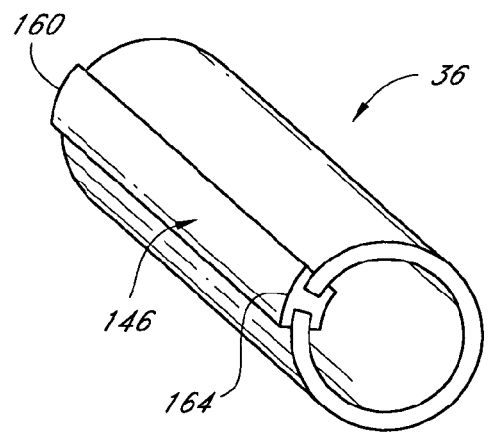

In another embodiment of the invention, shown in FIGS. 19A and 19B, the device 36 further comprises a spacer 146 that may be inserted into the longitudinal opening 42 of the device 36 to increase size of the lumen 40 and provide more space around the nerve root 28. A spacer 146 may be inserted after the device 36 is positioned in the intervertebral foramen 26. In one embodiment, the spacer 146 comprises an elongate body 148 generally having an H-shaped cross section, an outer height 150, an inter-edge height 152, an inner height 154, a first edge groove 156 and a second edge groove 158, an insertion end 160 and a trailing end 162. The inter-edge height 152 of the spacer 146 determines the separation between the edges 58, 60 of the device 36. In some embodiments, the outer height 150 of the elongate body 148 is about equal to the height of the inner height 154 of the elongate body 148. In other embodiments, the inner height 154 is different from the outer height 150, preferably having a reduced inner height 154 to decrease the amount volume taken by the spacer 146 in the lumen 40 of the device 36. In some embodiments, either the first edge groove 156 and/or the second edge groove 158 is configured with a cross-sectional configuration that is complementary to the cross sectional shape of the first edge 58 and/or second edge 60 of the device 36, respectively, to improve the fit of the spacer 146 to the device 36. In some embodiments, the complementary configuration of the device 36 and spacer 146 is an interlocking configuration.

Figure 20:
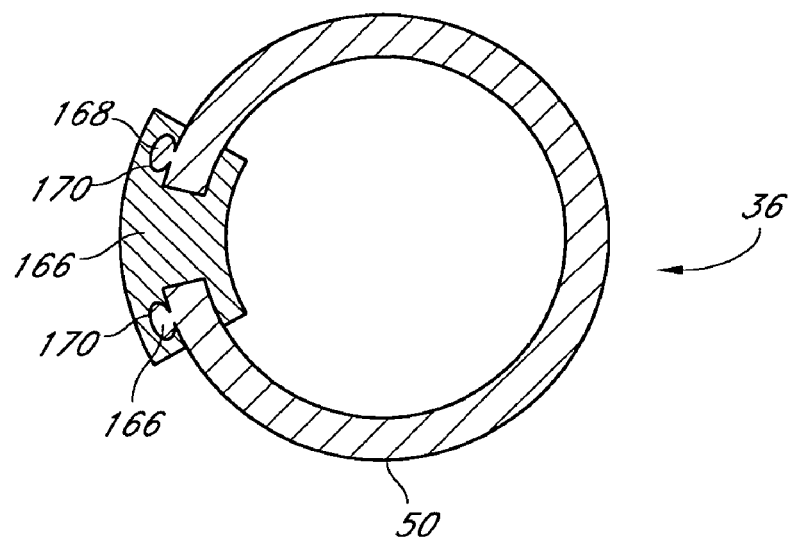
FIG. 20 is a cross sectional view of one embodiment of the invention comprising an interlocking spacer and device.
Figure 21:
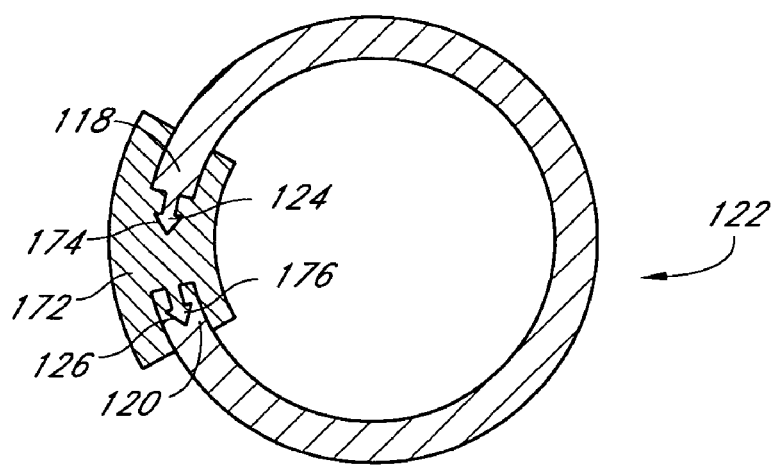
FIG. 21 is a cross sectional view of another embodiment of the invention comprising an interlocking spacer and device.

FIG. 20 depicts one embodiment of an interlocking configuration of the device 36 and spacer 166 comprising protrusions 168 on the abluminal surface 50 of the device 36 and complementary tracks 170 on the spacer 166. FIG. 21 depicts another embodiment where the male member 124 on the first edge 118 of the device 122 are capable of forming a snapfit with the second edge 120 of the device 120, or optionally a snapfit or sliding interlocking fit with a spacer 172 having a female receiving site 174 complementary to the male member 124 of the first edge 118 of the device 122 and a spacer male member 176 that is complementary to the female receiving site 126 on the second edge 120 of the device 122. One skilled in the art will understand that any of a variety of interlocking configurations and sites between the device 122 and spacer 172 may be used for the invention.

Figure 22A:
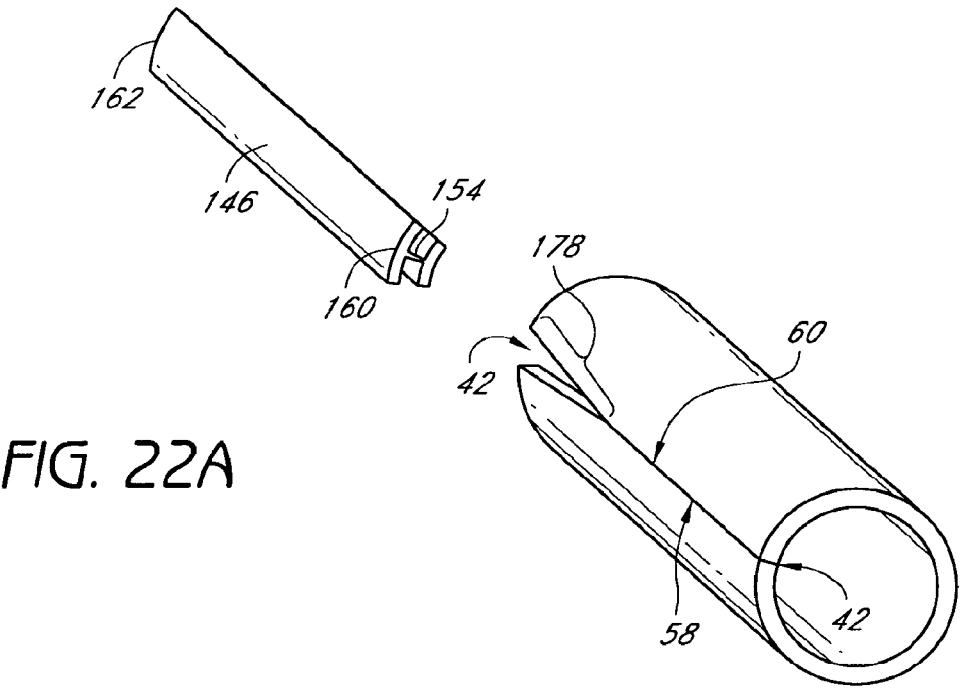
FIGS. 22A and 22B are oblique elevational views of a tapered spacer and a device with a widened gap region.
Figure 22B:
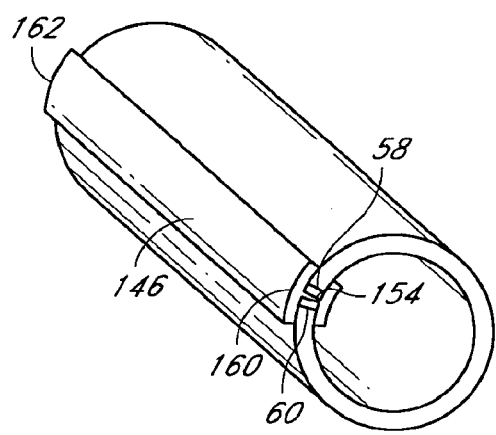

Referring to FIGS. 22A and 22B, in some embodiments, the inter-edge height 152 of the spacer 146 is tapered at least at the insertion end 160 of the spacer 146 to facilitate a gradual separation of the first and second edges 58, 60 of the device 36 as the spacer 146 is inserted into the longitudinal seam 42. In one embodiment, at least a portion of the longitudinal seam 42 at second end 48 of the device 36 has a tapered gap section 178 to facilitate insertion of the spacer 146 into the longitudinal seam 42.

Figure 23:
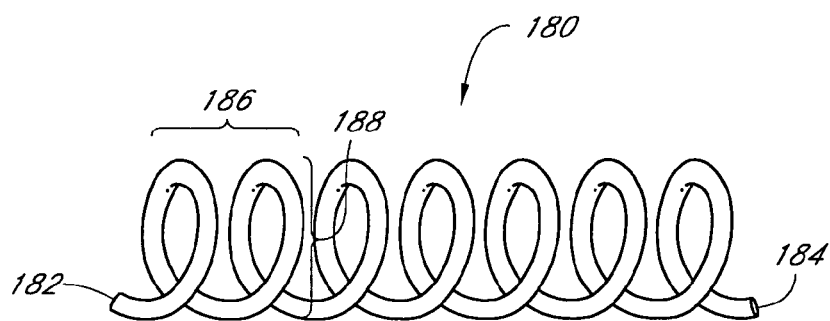
FIG. 23 depicts another embodiment comprising a spiral device
Figure 24:
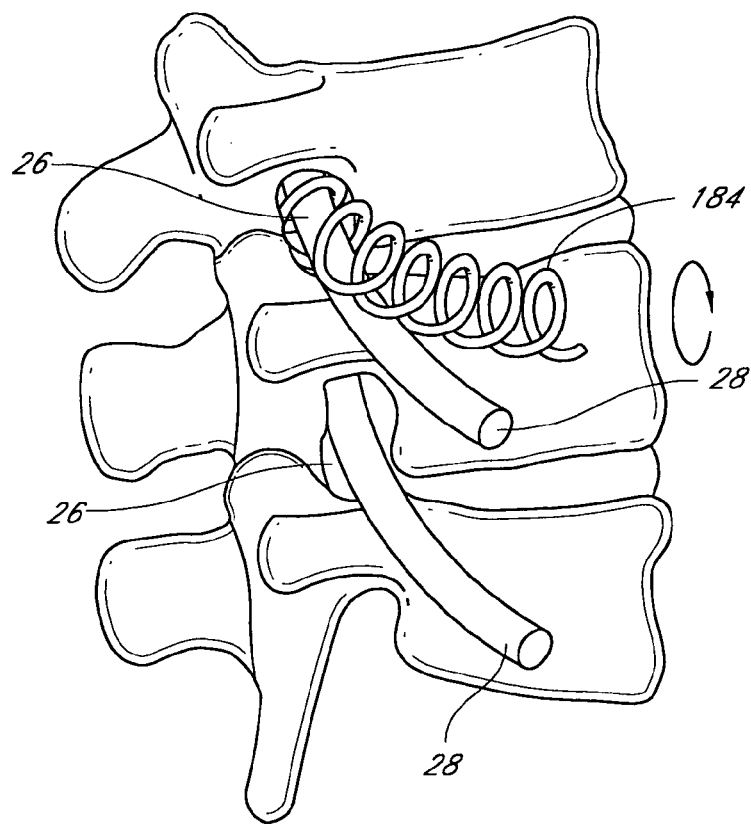
FIG. 24 is a schematic lateral elevational view of a portion of the vertebral column with the device of FIG. 23 inserted over a nerve root.

FIG. 23 depicts another embodiment of the invention comprising a spiral or coiled neuroprotective device 180 having an insertion end 182 and a trailing end 184 and adapted for insertion into the intervertebral foramen 26. The spacing 186 between each spiral 188 of the device 180 is configured to allow the isolated nerve root 28 to pass through the spacing 186 as the device 180 is twisted into the foramen 26. FIG. 24 illustrates how the device 180 is inserted into a foramen 26 and over the nerve root 28. The turn radius of the spirals 188 and the spacing 188 between each spiral 188 need not be uniform along the length of the device 180. In the preferred embodiment of the invention, the turn radius of the spirals at the insertion end 182 and/or trailing end 184 of the device 180 is larger to help maintain the device 180 in the intervertebral foramen 26.

The device 36 may comprise a polymer such as polyetheretherketone (PEEK), polyetherketoneketone (PEKK), or a fluropolymer, an elastomer, a ceramic such as zirconia, alumina or silicon nitride, a metal such as titanium, a titanium alloy, cobalt chromium or stainless steel, or a combination of these materials. In one embodiment, the device comprises a metallic frame embedded in a tubular polymer structure. In embodiments of the device 36 comprising a non-radioopaque material, radioopaque markers may be embedded in or on the device 36 to assist in placement or monitoring of the device 36 under radiographic visualization. In another embodiment, the device 36 may comprise a bioabsorbable or bioresorbable material that is known in the art. By selecting a particular configuration and material for the tubular body 38, one skilled in the art can adapt the device 36 to have the desired resiliency.

In some embodiments of the invention, the outer surface 50 of the device 36 may be further configured to provide one or more characteristics. In one embodiment, at least a portion of the abluminal surface 50 of the tubular body 38 comprises a porous layer for allowing bone ingrowth into the device 36. The porous layer may be formed by the application of sintered beads or plasma sprayed material onto the outer surface of the device 36. In other embodiments, the abluminal surface 50 may be laser treated or mechanically roughened to provide an irregular surface, or formed with protrusions or knurls, to resist sliding contact with bony surfaces contacting the device 36. In other embodiments, the luminal surface 50 may be polished or micropolished to facilitate insertion of the device into the foramen 26. A polished device 36 may rely on one or more flanges 118 to secure the device 36 in the foramen 26. The inner surface 52 of the device 36 may be similar treated as the outer surface, but in the preferred embodiment the inner surface 52 is polished or micropolished to reduce the risk of damage to the neural structures within the lumen 40 of the device 36.

The device 36 may also further comprise at least one drug-eluting region loaded with one or more treatment agents. The treatment agents may be any of a variety of treatment agents known in the art and include but are not limited to anti-bacterial agents, anti-inflammatory agents, anti-proliferative agents In one embodiment of the device, the intervertebral foramen 26 is accessed by an open procedure as is known by those with skill in the art. In some embodiments, the vertebrae 4 forming the foramen 26 are distracted along their longitudinal axis. The neural structure 28 is isolated and the device 36 is passed over the neural structure 28 through the longitudinal seam 42 within the intervertebral foramen 26. The placement of the device 36 may be performed in conjunction with orthopedic spine procedures, if any. The device 36 is optionally attached to one or more vertebrae 4 if the device 36 has at least one flange 118 with an attachment opening 120. The distraction force, if any, is removed from the vertebrae 4 and the surgical site is closed.

In another embodiment, the intervertebral foramen 26 is accessed in a minimally invasive manner. In one embodiment, injection of radio-opaque dye is used to identify the vertebrae 4, foramen 26 and neural structures 28. In another embodiment, positioning markers may be placed about the vertebral column 2 to assist in localizing the spinal structures. The vertebrae 4 forming the foramen 26 are optionally distracted along their longitudinal axis to enlarge the foramen 26 during the procedure. The neural structure 28 is isolated and the device 36 is passed over the neural structure 28 through the longitudinal opening 42 within the intervertebral foramen 26 in conjunction with any other orthopedic spine procedures, if any. The device 36 is optionally attached to one or more vertebrae 4 if the device 36 has at least one flange 118 with an attachment opening 120. The distraction force, if any, is removed from the vertebrae 4 and the surgical site is closed.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A device for treating the spine, comprising:
    a tubular body comprising a first end, a second end, an abluminal surface, a luminal surface, a lumen, a first edge, a second edge, a hinge region, and a flange extending radially from the abluminal surface along a primary axis substantially perpendicular to a longitudinal axis of the tubular body from a location along a length of the tubular body between the first end and the second end such that an interface between the flange and the tubular body forms an arch;
    wherein the tubular body is adapted for positioning within an intervertebral foramen.

2. The device for treating the spine as in claim 1, wherein the flange comprises one or more through lumens adapted for accepting a bone screw.

3. The device for treating the spine as in claim 2, wherein the flange comprises one or more through openings adapted for accepting a bone screw.

4. The device for treating the spine as in claim 1, wherein the tubular body comprises a material selected from the group consisting of polymers, polyetheretherketone (PEEK), polyetherketoneketone (PEKK), polyethylene, fluoropolymers, elastomers, ceramics, zirconia, alumina, silicon nitride; metal(s), titanium, titanium alloy, cobalt chromium, stainless steel, and combinations of these materials.

5. The device for treating the spine as in claim 1, wherein the hinge region comprises at least one region of reduced wall thickness on the tubular body.

6. The device for treating the spine as in claim 5, wherein the hinge region extends the full length of the tubular body between the first end and the second end.

7. The device for treating the spine as in claim 5, wherein the hinge region is located around 180 degrees opposite the first edge and the second edge.

8. The device for treating the spine as in claim 1, wherein the flange comprises a material or configuration such that the flange may at least partially conform to a bony structure to which it is attached.

9. The device for treating the spine as in claim 1, wherein the flange is adapted to maintain the device at a desired location in the intervertebral foramen by its configuration alone, without attachment to a bony structure.

10. A device for treating the spine, comprising:
    a tubular body comprising a first end, a second end, an abluminal surface, a luminal surface, a lumen adapted for accepting a nerve, a first edge, and a second edge; and
    a flange comprising a first surface generally facing the first end of the tubular body, a second surface generally facing the second end of the tubular body, wherein the first and second surfaces are the largest surfaces of the flange, and at least one lumen connecting the first and second surface adapted for receiving a bone fastener;
    wherein the tubular body is adapted for positioning within an intervertebral foramen; and
    wherein the tubular body comprises a material selected from the group consisting of polymers, polyetheretherketone (PEEK), polyetherketoneketone (PEKK), polyethylene, fluoropolymers, elastomers, ceramics, zirconia, alumina, silicon nitride; metal(s), titanium, titanium alloy, cobalt chromium, stainless steel, and combinations of these materials.

11. The device for treating the spine as in claim 10, wherein the tubular body further comprises a hinge region.

12. A device for treating the spine, comprising:
    a tubular body comprising a first end, a second end, a first edge and a second edge defining a longitudinal opening along the tubular body and wherein the tubular body is adapted for positioning within an intervertebral foramen; and
    a flame extending radially from a surface of the tubular body such that an interface between the flange and the tubular body forms an arch over a portion of a circumference of the tubular body and the flame interfaces with the tubular body at a position between and separated from the first end and the second end of the tubular body;
    wherein the tubular body is configured to resist narrowing or closure of the longitudinal opening along the length of the tubular body after implantation.

13. The device for treating the spine as in claim 12, wherein the tubular body is a stent structure.

14. The device for treating the spine as in claim 12, wherein the tubular body is configured to resist compression forces from an intervertebral disc.

15. The device for treating the spine as in claim 12, wherein the tubular body is configured to resist compression forces from a vertebra.

16. A device for treating the spine, comprising:
- a tubular body comprising a first end, a second end, and a length between the first end and the second end, wherein the tubular body is adapted for positioning within an intervertebral foramen;
- a flange arising radially from the tubular body and comprising a first surface generally facing the first end of the tubular body, a second surface generally facing the second end of the tubular body, wherein the first and second surfaces are the largest surfaces of the flange,
- wherein the flange is located at a position along the length of the tubular body such that the distance between the flange and the first end is equal to a desired insertion depth of the tubular body within the intervertebral foramen and
- wherein, on insertion of the tubular body to the desired insertion depth within the intervertebral foramen, the flange contacts a bony structure and maintains the device at the desired insertion depth.

* * * * *

UNITED STATES PATENT AND TRADEMARK OFFICE
CERTIFICATE OF CORRECTION

| | |
|---|---|
| PATENT NO. | : 8,500,763 B2 |
| APPLICATION NO. | : 12/782002 |
| DATED | : August 6, 2013 |
| INVENTOR(S) | : Blain |

It is certified that error appears in the above-identified patent and that said Letters Patent is hereby corrected as shown below:

On the Title Page

In column 1 (page 1 item 73) at line 1, Change "Spinal Elemtents, Inc.," to --Spinal Elements, Inc.,--.

In the Claims

In column 10 at line 51, In Claim 12, change "flame" to --flange--.

Signed and Sealed this
Eighteenth Day of February, 2014

Michelle K. Lee
*Deputy Director of the United States Patent and Trademark Office*